United States Patent [19]

Moorhouse

[11] Patent Number: 5,991,915
[45] Date of Patent: *Nov. 30, 1999

[54] PROTECTIVE HEADWEAR ARTICLE

[76] Inventor: Gerard Maxwell Moorhouse, 1628 Crabtree Road, Grove, Tasmania, Australia, 7106

[*] Notice: This patent issued on a continued prosecution application filed under 37 CFR 1.53(d), and is subject to the twenty year patent term provisions of 35 U.S.C. 154(a)(2).

[21] Appl. No.: 08/676,254
[22] PCT Filed: Jan. 17, 1995
[86] PCT No.: PCT/AU95/00021
§ 371 Date: Jul. 17, 1996
§ 102(e) Date: Jul. 17, 1996
[87] PCT Pub. No.: WO95/19157
PCT Pub. Date: Jul. 20, 1995

[30] Foreign Application Priority Data

Jan. 17, 1994 [AU] Australia .................................. 3383

[51] Int. Cl.$^6$ ............................................ A41D 13/00
[52] U.S. Cl. .................................... 2/12; 2/9; 2/909
[58] Field of Search ...................... 2/12, 9, 909, 918

[56] References Cited

U.S. PATENT DOCUMENTS

| | | |
|---|---|---|
| D. 302,609 | 8/1989 | Wheeler . |
| D. 329,444 | 9/1992 | Rauch . |
| D. 354,588 | 1/1995 | Russell . |
| 1,803,338 | 5/1931 | Magee . |
| 2,060,127 | 11/1936 | Schofield . |
| 3,214,767 | 11/1965 | Weber ............................... 2/9 |
| 3,383,707 | 5/1968 | McNeil ............................. 2/12 |
| 3,389,406 | 6/1968 | Mitchell . |
| 3,952,331 | 4/1976 | Melville ............................ 2/9 |
| 4,096,589 | 6/1978 | Goldstein . |
| 4,258,437 | 3/1981 | Sawatsky ......................... 2/12 |
| 4,393,519 | 7/1983 | Nicastro ........................... 2/12 |
| 4,547,903 | 10/1985 | Brown et al. .................... 2/12 |
| 4,825,878 | 5/1989 | Kuntz et al. . |
| 4,853,974 | 8/1989 | Olin .................................. 2/9 |
| 4,955,087 | 9/1990 | Perez et al. ................... 2/909 |
| 5,105,476 | 4/1992 | Cox . |
| 5,245,709 | 9/1993 | Shipcott ........................... 2/9 |
| 5,365,615 | 11/1994 | Pigzkin ........................... 2/12 |

FOREIGN PATENT DOCUMENTS

| | | |
|---|---|---|
| 6372/46 | 3/1950 | Australia . |
| 70182/87 | 9/1987 | Australia . |
| 428985 | 5/1935 | United Kingdom . |

*Primary Examiner*—Bibhu Mohanty
*Attorney, Agent, or Firm*—McDermott, Will & Emery

[57] ABSTRACT

A protective article for use as headwear including: a flexible support (4) and a shield (2) able to be removably secured to the flexible support (4), wherein both the flexible support (4) and the shield (2) are of a substantially flat configuration, and in use, the flexible support (4) is able to be configured to surround the forehead of a user, and the shield (2) is able to be configured to shield the eyes of the user.

11 Claims, 1 Drawing Sheet

PROTECTIVE HEADWEAR ARTICLE

FIELD OF THE INVENTION

The present invention relates to a protective article, particularly a protective article that may be used as headwear. The article is particularly applicable for protecting a person who may be wearing the article, from facial injuries including injuries to the eye, eyebrow region and temple region, while playing sport.

The article is most appropriate for use while playing games such as squash, racquet-ball, badminton, and other games where there is the potential for facial injuries due to ball or equipment contact. The potential for serious eye, face and head injury is well recognized whilst playing such games, particularly for lesser skilled "social players" and children.

SUMMARY OF THE INVENTION

A variety of particular spectacles, goggles or other protective equipment has been utilized, particularly for the game of squash and racquet-ball, however none have proven to be particularly satisfactory for various reasons. For examples, spectacles or goggles tend to fog up as sweat runs down the inside of the lenses. Lighting may also be problem where spectacles or goggles are worn as the light can flare up. The protective device may also dislodge, or become uncomfortable to wear during play if it is not securely affixed to the user.

A particular problem with known spectacles and goggles, is that it is generally not possible for players who already wear spectacles to wear such protective equipment. Such players may generally rely upon their own spectacles for protection, however such spectacles are likely to shatter if struck firmly which may be more dangerous that wearing no protection equipment at all. At the very least, such glasses will dislodge readily.

The present invention aims to overcome or at least alleviate one or more of the difficulties associated with the prior art.

The present invention resides in a protective article for use as headwear including;
a flexible support, and
a shield able to be removably secured to the flexible support;
wherein both the flexible support and the shield are of a substantially flat configuration, and in use, the flexible support is able to be configured to surround the forehead of a user, and the shield is able to be configured to shield the eyes of the user.

The flexible support is generally of an elongated configuration and should be suitably flexible to enable it to be positioned around the forehead of the user. In this respect, the flexible support may have some form of adjustable connecting means so that it is able to connect behind the head of the user. Adjustment of the connecting means will enable the article to fit firmly around the head. Placing the flexible support around the head defines an inner surface of the flexible support against the head of the user, and an outer surface.

The flexible support is most preferably made of a strong light plastics material. Most suitably it has been found that a construction of a composite carbon fibre plastics material achieves the desired characteristics of the flexible support. That is, this material is particularly strong while still being flexible and lightweight.

The connecting means for the flexible support, may consist of a commonly used clasp, attached to either end of the flexible support by elastic straps. The elastic straps provide a comfort for the user, as well as ensuring there is a secure fit.

Most preferably, the protective article includes a padded insert that is able to be removably secured to the inner surface of the flexible support. The padded inserts primary function is to provide cushioning and comfort for the user. In use, the padded insert preferably extends from one temple of the user to the other, the cushioning providing protection for the user in the temple region and along the forehead and eyebrow region. The cushioning is able to absorb any accidental blows in these areas.

A secondary function of the padded insert is to absorb moisture and preferably includes a moisture absorbent covering. A preferred construction of the padded insert is a rubber material, such as neoprene, covered by towelling. The padded insert is therefore able to absorb sweat and prevent moisture from running into the eyes or onto the shield or other glasses of the user.

The padded insert should be removably secured to the flexible support in order that it may be removed for separate storage or cleaning. A suitable means for securing the padded insert to the flexible support is by means of a velcro™ strip on both the inner surface of the flexible support and on the padded insert.

The padded insert may comprise more than one insert strategically positioned so as to provide adequate protection and to secure and support spectacle frames. That is, the insert may consist of specific temple inserts and a separate insert across the forehead of the user. Most preferably, the insert consists of a single piece.

The shield of the protective article should also be of a clear plastics material. A suitable material is perspex or other such clear plastic material. Particularly preferred is a composite carbon fibre plastics material. In some circumstances it may be appropriate that the shield is tinted for example where it may be used in bright lighting or outdoor use.

As an alternative, the shield may also consist of vertical bars, created by cutting out certain sections of a flat shield. This configuration allows for an increase in ventilation through the shield. The user will not focus on the bars in use, due to the close proximity to the face. In this form the shield should be made of a stronger material such as a composite carbon fibre plastics material.

The shield should include securing means to enable it to be removably secured to the flexible support. The shield itself is generally of a longitudinal flat configuration, and the securing means generally includes holes located in either end of the shield. The holes should correspond with a key arrangement on the outer surface of the flexible support.

The holes on the shield should be separated by a distance greater than the key arrangement on the flexible support. In use, this will cause the shield to flex at a greater angle than the flexible support ensuring that the shield protrudes slightly from the face of user and from the flexible support. This provides the added benefit of ventilation between the face of the user and the shield assisting in preventing the shield from "fogging up" during use. It also enables the shield to protrude over the nose of the user, and may be adapted to provide adequate protection for the nose. The shield could even be extended to shield the entire face if necessary. It has also been found that the shield will generally increase in strength when in a flexed position.

The arrangement of the protective article of the present invention provides many advantages over existing prior art.

A particular advantage of the present invention is that its components are readily detached from each other to enable separate cleaning and storage of each component, and replacement should this be necessary.

The flat configuration of each component enables the protective article to be stored easily. This has benefit for the owners of sporting complexes that may store the equipment and to the individual user when bringing his or her own equipment to be used.

The protective article of the invention further has the advantage of protecting not only the eyes of the user, but also other areas of the head such as the forehead, temple and eyebrow region.

A further advantage is that, as the article is able to be secured firmly to the head of the user, if the user is wearing spectacles, the article is able to hold those glasses in position during play.

BRIEF DESCRIPTION OF THE DRAWINGS

The present invention will now be described with reference to the accompanying drawings. It should be appreciated that these drawings are merely illustrative of the present invention and that the present invention should not be considered to be limited thereto.

DESCRIPTION OF THE PREFERRED EMBODIMENTS

Figure 1:
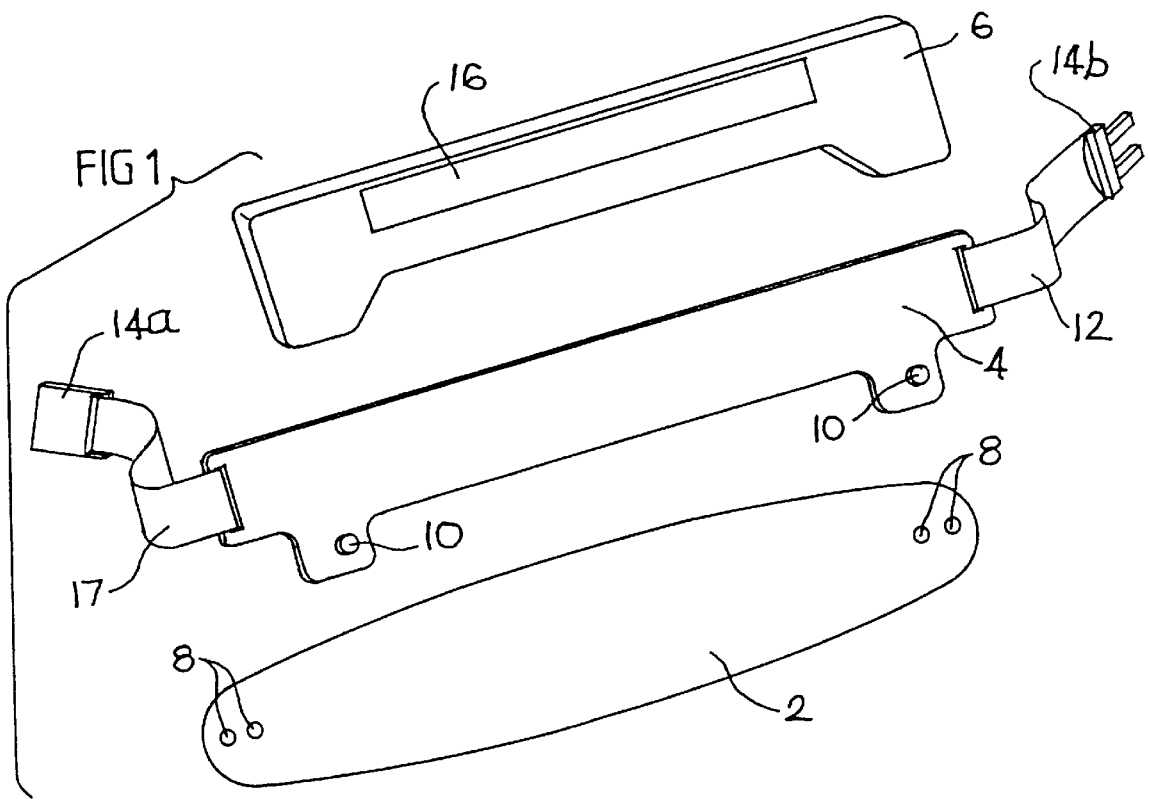
FIG. 1 illustrates a perspective view of each of the components of the protective article of the invention.

FIG. 1 illustrates the article separated into its various components with a shield (2), a flexible support (4), and a padded insert (6). Each of the components is of a substantially flat configuration when not in use and may be stored an maintained separately.

The shield (2) is of a substantially elongate configuration having holes (8) at either end of the shield. The shield is of a clear plastics material and is of such a size to adequately shield the eyes of a user in use. The shield includes a plurality of holes to allow for appropriate adjustment.

The flexible support is also of a substantially elongate configuration, and includes key members (10) at either end of the flexible support to assist in securing the shield to the flexible support. The holes in the shield simply slot over the key member of the flexible support. The flexible support also includes elastic straps (12) with a clasp (14a) and (14b) at either end to enable the flexible support to be secured around the head of the user.

The distance between the key members (10) of the flexible support is slightly less than the distance between the holes (8) on the shield. In use, this enables the shield to be configured so that it protrudes slightly from the flexible support keeping it away from the face of the user. This is better illustrated in FIG. 2.

The padded insert (6) consists of a rubber material surrounded by towelling. It includes a velcro strip (16) which enables it to be readily affixed to a corresponding strip (not shown) on the inner surface of the flexible support.

Figure 2:
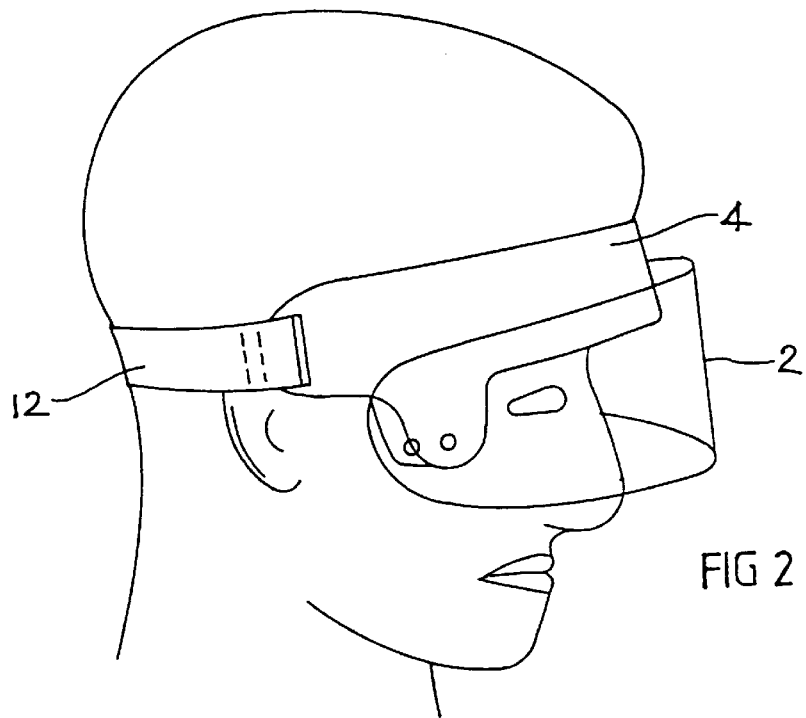
FIG. 2 illustrates a view of the protective article as it may be used.

FIG. 2 illustrates the protective article of the invention in use. This demonstrates how the shield protrudes from the face when the protective article is affixed around the head of the user. The shield and flexible support are configured such that the shield is flexed to adequately cover the eyes of the user while the flexible support and the padded insert are configured and placed to provide protection along the forehead, eyebrow and temple region of the user.

Finally, it will be appreciated that many variations, modifications and alterations may be made to the above described article without departing from the spirit or ambit of the present invention. It should be considered that the description encompasses these variations.

I claim:

1. A protective headwear article comprising:
    a flexible support having at least two protruding members extending from an outer surface thereof;
    a padded insert removably secured to an inner surface of said flexible support; and
    a shield having at least two apertures adapted to removably receive said at least two protruding members therein,
    wherein said inner surface of said flexible support is adapted to surround a head of a user and said shield is adapted to protect a face of the user from impact during sporting events.

2. The protective headwear article of claim 1 wherein said shield is constructed of a composite carbon fiber plastics material.

3. The protective headwear article of claim 1 wherein said padded insert includes a moisture absorbent cover having a hook and loop strip to affix said padded insert to a corresponding hook and loop strip on said inner surface of said flexible support.

4. The protective headwear article of claim 1 wherein said padded insert includes cushioning material extending from one temple of the user to an opposite temple of the user.

5. The protective headwear article of claim 1 wherein said flexible support, said padded insert, and said shield are of a substantially flat configuration along respective lengths thereof when not in use, and wherein said flexible support and said shield are of a curved configuration when in use.

6. The protective headwear article of claim 1 wherein said at least two apertures in said shield are spaced apart by a greater distance than said at least two protruding members of said flexible support such that when in use said shield will protrude slightly from said flexible support, when said shield is locked to said flexible support.

7. The protective headwear article of claim 1 further comprising an adjustable elastic strap removably secured to said flexible support.

8. The protective headwear article of claim 1 wherein said flexible support has opposing ends that are removably connected when said protective headwear article is in use to curve said flexible support along its length.

9. The protective headwear article of claim 8 wherein said flexible support has straps at said opposing ends, said straps having ends that are adapted to couple together.

10. The protective headwear article of claim 1 wherein said shield has two sets of said at least two apertures adapted to removably receive said at least two protruding members therein.

11. The protective headwear article of claim 1 wherein said flexible support includes a downwardly extending portion that extends over a portion of a temple region of the user, said at least two protruding members extending from said downwardly extending portion.

* * * * *